US008114085B2

(12) United States Patent
von Jako

(10) Patent No.: US 8,114,085 B2
(45) Date of Patent: Feb. 14, 2012

(54) PERCUTANEOUS REGISTRATION-AND-ACCESS TOOL FOR MINIMALLY INVASIVE SPINAL SURGERY

(75) Inventor: Ronald A. von Jako, Lawrence, MA (US)

(73) Assignee: General Electric Company, Schenectady, NY (US)

( * ) Notice: Subject to any disclaimer, the term of this patent is extended or adjusted under 35 U.S.C. 154(b) by 80 days.

(21) Appl. No.: 11/279,719

(22) Filed: Apr. 13, 2006

(65) Prior Publication Data

US 2007/0270866 A1   Nov. 22, 2007

(51) Int. Cl.
*A61B 17/70* (2006.01)
(52) U.S. Cl. .................. 606/86 A; 606/190; 600/218
(58) Field of Classification Search ............ 606/86, 606/184, 186, 190, 191, 86 A; 604/164.01, 604/164.04, 164.11, 175, 264; 600/211–220
See application file for complete search history.

(56) References Cited

U.S. PATENT DOCUMENTS

| | | | | |
|---|---|---|---|---|
| 1,680,490 A * | 8/1928 | Wappler | | 600/104 |
| 4,296,786 A * | 10/1981 | Brignola | | 141/309 |
| 4,585,437 A * | 4/1986 | Simms | | 604/106 |
| 5,368,573 A * | 11/1994 | Andrew | | 604/158 |
| 5,391,156 A * | 2/1995 | Hildwein et al. | | 604/174 |
| 5,404,870 A * | 4/1995 | Brinkerhoff et al. | | 600/184 |
| 5,433,739 A * | 7/1995 | Sluijter et al. | | 607/99 |
| 5,514,148 A * | 5/1996 | Smith, III | | 606/151 |
| 5,776,110 A * | 7/1998 | Guy et al. | | 604/264 |
| 5,938,680 A * | 8/1999 | Ginn | | 606/190 |
| 5,976,146 A * | 11/1999 | Ogawa et al. | | 606/86 |
| 6,080,155 A * | 6/2000 | Michelson | | 606/60 |
| 6,226,548 B1 | 5/2001 | Foley et al. | | |
| 6,371,968 B1 * | 4/2002 | Kogasaka et al. | | 606/190 |
| 6,755,815 B2 * | 6/2004 | Schultz | | 606/1 |
| 7,179,261 B2 * | 2/2007 | Sicvol et al. | | 606/73 |
| 2002/0004351 A1 * | 1/2002 | Nobbee et al. | | 442/394 |
| 2004/0133229 A1 * | 7/2004 | Lambrecht et al. | | 606/190 |
| 2005/0080418 A1 * | 4/2005 | Simonson et al. | | 606/61 |
| 2005/0277832 A1 | 12/2005 | Foley et al. | | |
| 2006/0009780 A1 | 1/2006 | Foley et al. | | |
| 2006/0142643 A1 * | 6/2006 | Parker | | 600/219 |
| 2007/0027364 A1 * | 2/2007 | Schwer | | 600/219 |
| 2007/0032790 A1 * | 2/2007 | Aschmann et al. | | 606/61 |
| 2007/0260125 A1 * | 11/2007 | Strauss et al. | | 600/219 |
| 2007/0276190 A1 * | 11/2007 | Tsahakis | | 600/210 |
| 2007/0276370 A1 * | 11/2007 | Altarac et al. | | 606/61 |

FOREIGN PATENT DOCUMENTS

EP   0890341 A1   1/1999

* cited by examiner

*Primary Examiner* — Eduardo C Robert
*Assistant Examiner* — Jan Christopher Merene

(57) ABSTRACT

Described herein is one or more implementations for a percutaneous spinal registration-and-access tool for minimally invasive spinal surgery involving lumbar pedicle screw fixation and registration (which is the set-up process for spinal computer navigation). This spinal registration-and-access tool aids registration by allowing more precise targeting of the spinous process (of the vertebrae) and safe working channel for percutaneous placement of a sharp tool (e.g., a bone pin) through the protected subcutaneous tissue.

12 Claims, 3 Drawing Sheets

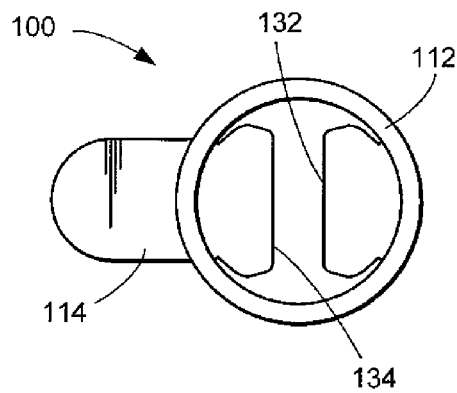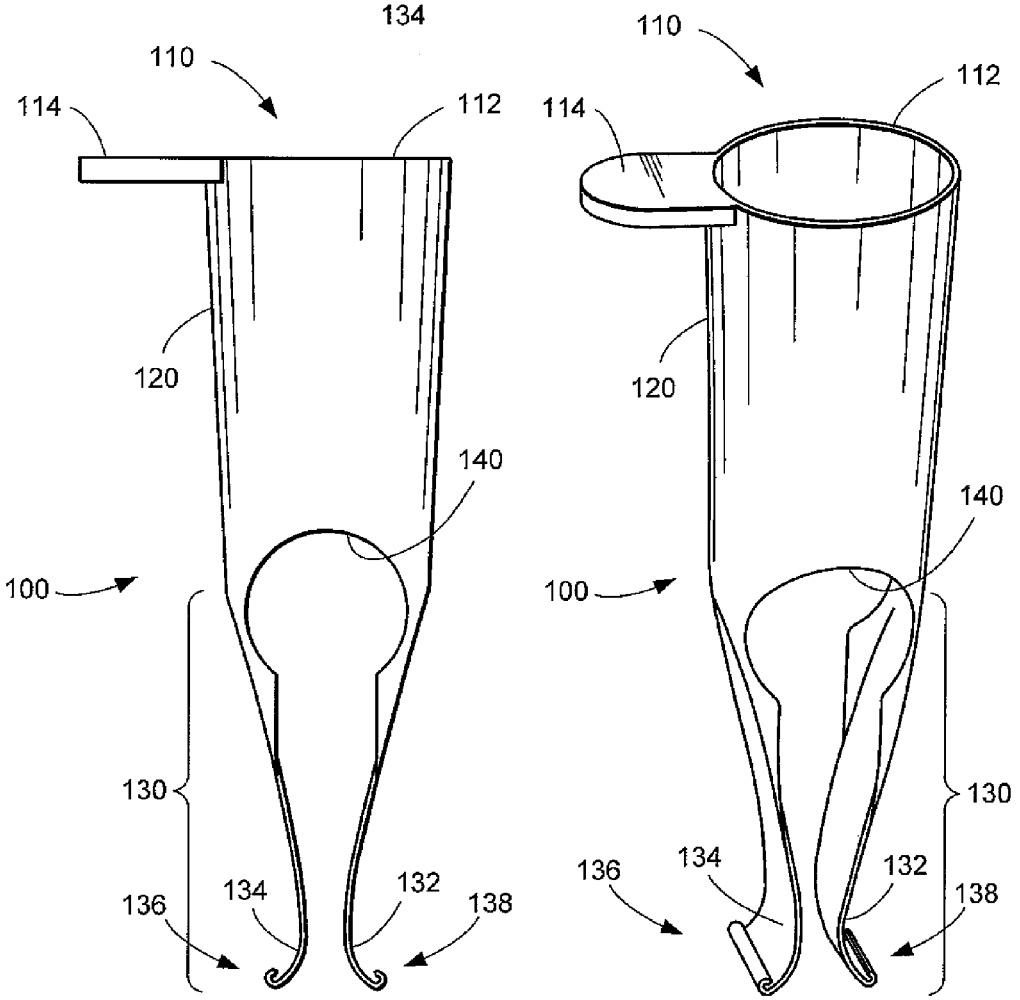

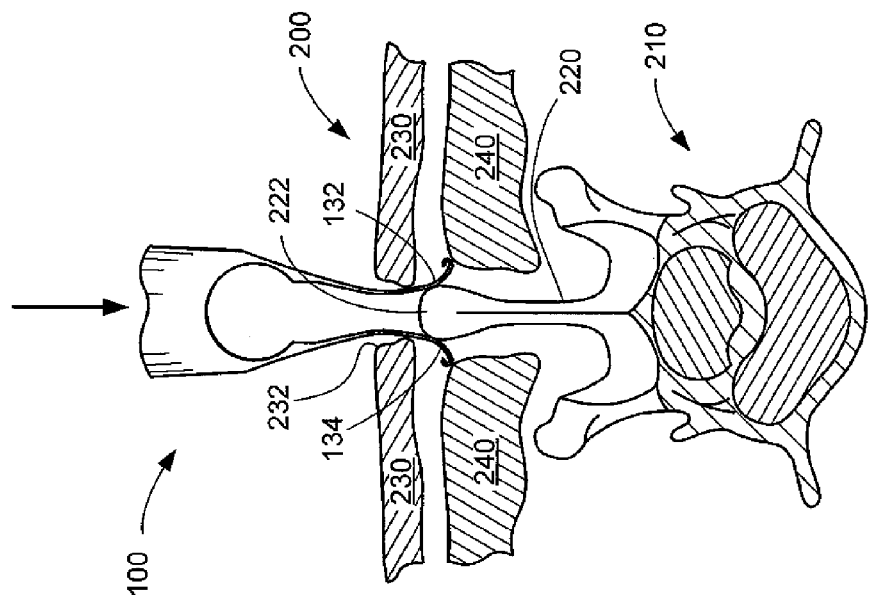
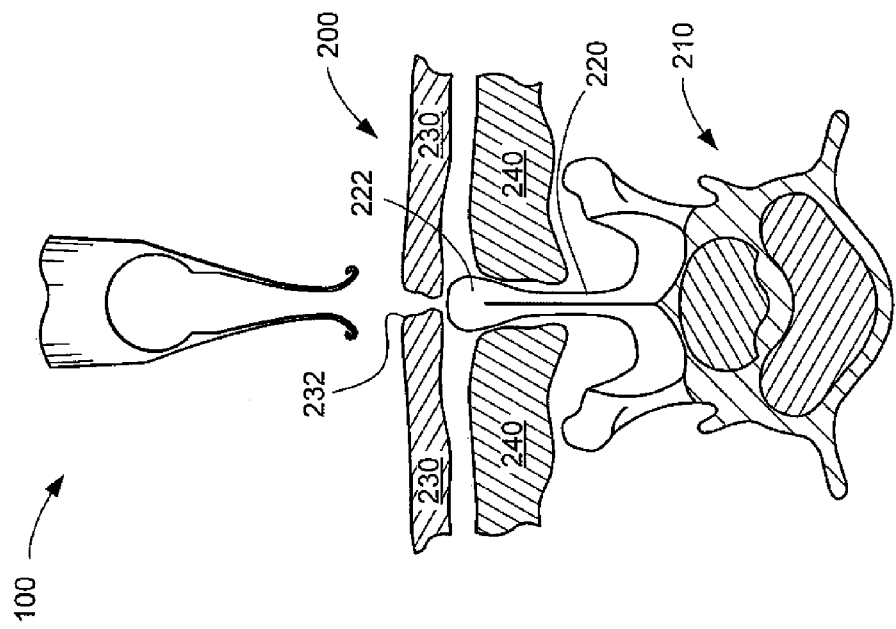

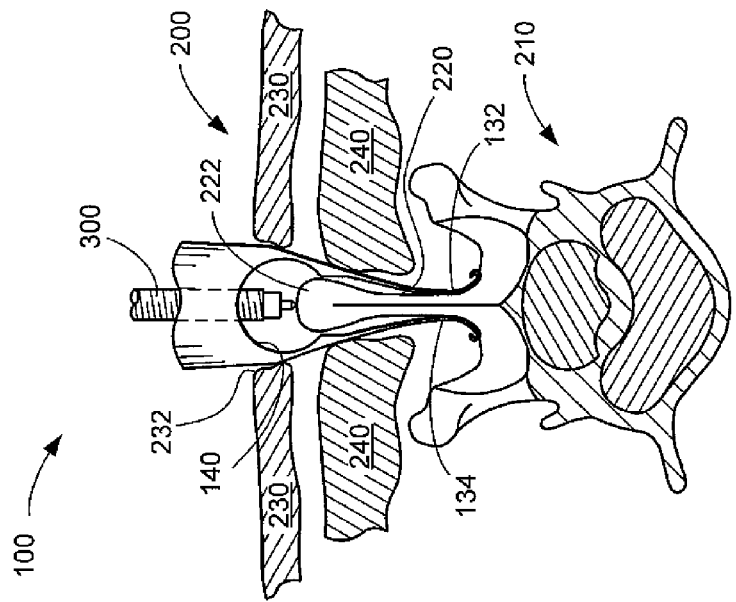
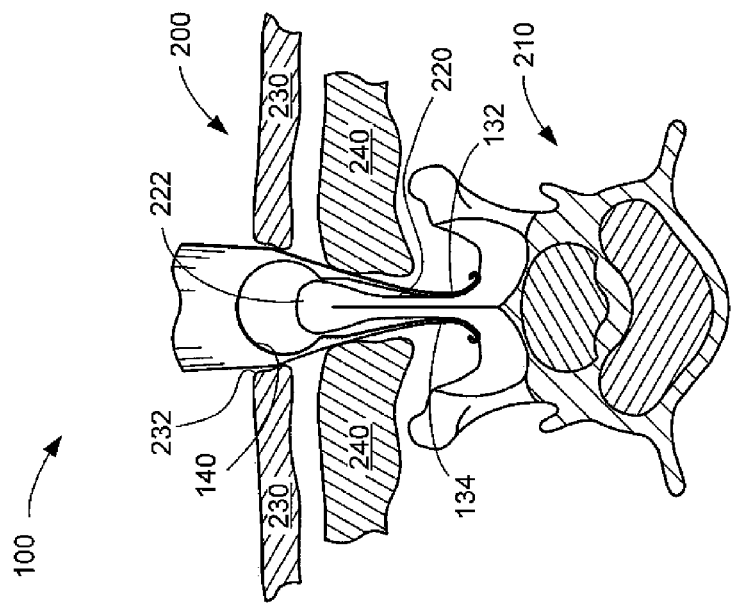
FIG. 6
FIG. 7

PERCUTANEOUS REGISTRATION-AND-ACCESS TOOL FOR MINIMALLY INVASIVE SPINAL SURGERY

BACKGROUND

In spinal surgery, implant screws or "pedicle screws" are often utilized to stabilize the spine. Typically, these pedicle screws are driven through the pedicles and connected adjacently by rods to manipulate and stabilize the spine during fusion between the bony segments of the spine. Pedicles are two cylindrical or ovoid bones that extend posteriorly from the dorsal surface of the vertebral bodies. Placing these implant screws is typically referred to as "lumbar pedicle screw fixation." Conventional technique for lumbar pedicle screw fixation involves an open exposure and expanded muscle dissection in order for the surgeon to have a clear and unobstructed access to the spine.

During a back surgery that targets these lumbar pedicles, the entry point into the back is open and exposed. This exposure may lead to extensive blood loss, muscle disruption, post-operative morbidity, lengthy hospital stays, recovery and/or significant costs. In response to this, spinal surgeons and industry have developed minimally invasive surgical (MIS) techniques and technologies, such as posterior fixation delivery devices that enable percutaneous (i.e., "effected or performed through the skin") placement of pedicle screws and rods.

MIS spine techniques do offer significant benefits over traditional spinal approaches. These benefits include reduction in the blood loss, smaller incisions, muscle sparring approaches, shorter hospital stays, and similar to less complications in well experienced institutions. However, MIS techniques also reduce the visibility of the surgical field and thus make it more difficult for the surgeon to directly visualize the anatomy.

Consequently, when using MIS techniques, surgeons often rely on live fluoroscopic guidance or other equivalent surgical navigation tools. With fluoroscopic X-ray guidance, a surgeon can see the internal structure of opaque objects (such as the living body) by means of the shadow cast by the object examined upon a fluorescent screen when placed between the screen and a source of X-rays. In modern surgery, it's the use of an intraoperative fluoroscope, commonly referred to as a C-arm for real-time x-ray image updates.

Dependence on fluoroscopic guidance for MIS techniques may lead to increased fluoroscopic times. This means that the patients, the surgeon (especially his-hands, and OR staff are exposed to increased levels of X-ray radiation). Moreover, in order to produce these two-dimensional or even three-dimensional views of the anatomy in single or multiple planes, "snapshots" or control shots may be frequently used. Doing this also increases the X-ray-exposure time. In addition, there are other ergonomic challenges with a "C-arm" (fluoroscopic guidance) and these challenges increase the X-ray exposure and risks of contamination to the sterile field.

To enhance and enable these least invasive approaches while minimizing the radiation and sterilization exposure risks, "virtual fluoroscopy" technology can often be employed. Virtual fluoroscopy technology uses calibration and tracking sensor devices that attach to both the C-arm and the patient. The surgeon then prepares to perform a lumbar pedicle screw fusion for target regions of the spine. To prepare for navigation, first a reference "sensor" device is attached to the spinous process via a bone pin or clamp. This is performed through an existing or additional small incision in the back for MIS procedures. The incision in open procedures must be spread wide enough for the surgeon to see, guide, and place both the reference sensor and the implant screws into the pedicles. For MIS pedicle screw procedures, the incision is small and requires x-ray targeting to the spine, but when surgical navigation is deployed, incremental fluoroscopic updates are significantly reduced.

A transmitter is connected to the previously attached reference bone pin or clamp and the surgeon takes and saves to the computer typically two or more different fluoroscopic X-ray views. The calibration device and navigation computer automatically registers the images to the patient's anatomy. During the MIS procedure, the surgeon is able to use these saved and calibrated images to plan trajectories, locate difficult anatomy, and determine other surgical parameters in near real-time using virtual instruments superimposed over the previously saved images, with out the need for continuous updated fluoroscopic shots. In addition to improved accuracy in multi-view tracking, one key benefit of virtual fluoroscopy is reduced x-radiation dose for the patient and the surgical team, since the need for continuous fluoroscopy is eliminated.

Conventional approaches to lumbar pedicle screw fixation often require a significant incision and spreading of the open tissue for the surgeon to see the exposed spine and effectively implant the pedicle screw into the spine. In contrast, less invasive percutaneous approaches for MIS requires small key-hole like incisions through the tissue. The rough or sharp edges of the exposed portions of the specific reference pin or screw for the reference transmitter (sensor), can be difficult to place to the target bone by poor direct visualization and may injure this surrounding subcutaneous tissue during placement. In the end, after the surgery, additional injury may be possible to the surrounding tissue by the removal of the fixated reference screw or pin used to hold the reference transmitter (sensor). It is desirable to make these aspects of a nominally minimally invasive technique to be even less invasive. The patient benefits from doing so are by further reduction in the blood loss, tissue trauma, placement and removal times, medication, quicker discharge, and reduced complications.

SUMMARY

Described herein are one or more implementations for a percutaneous spinal registration-and-access tool for minimally invasive spinal surgery involving lumbar pedicle screw fixation and registration (which is the set-up process for spinal computer navigation). This spinal registration-and-access tool aids registration by allowing more precise targeting of the spinous process (of the vertebrae) and a safe working channel for percutaneous placement of a sharp tool (e.g., a bone pin) through the access tool that protects the surrounding subcutaneous tissue.

This summary itself is not intended to limit the scope of this patent and the appending claims of this patent. Moreover, the title of this patent is not intended to limit the scope of this patent. For a better understanding of the present invention, please see the following detailed description and appending claims, taken in conjunction with the accompanying drawings. The scope of the present invention is pointed out in the appending claims.

BRIEF DESCRIPTION OF THE DRAWINGS

The same numbers are used throughout the drawings to reference like elements and features.

FIG. 1 a top view of a percutaneous spinal registration-and-access tool in accordance with one or more implementations described herein.

FIG. 2 is an elevation view of a percutaneous spinal registration-and-access tool in accordance with one or more implementations described herein.

FIG. 3 is an isometric view of a percutaneous spinal registration-and-access tool in accordance with one or more implementations described herein.

FIG. 4 illustrates an elevation view of a cut-away lower portion of a percutaneous spinal registration-and-access tool in accordance with one or more implementations described herein and a cross-section view of a vertebrae—particularly, the spinous process—and a cross-section of some of the tissue surrounding the spinous process.

FIG. 5 illustrates the same elements depicted in FIG. 4. In accordance with one or more implementations described herein, the tool is shown being inserted through an incision and over the spinous process.

FIG. 6 illustrates the same elements depicted in FIGS. 4 and 5. In accordance with one or more implementations described herein, the tool is shown seated onto and over the spinous process.

FIG. 7 illustrates the same elements depicted in FIGS. 4 through 6 and a bone pin. In accordance with one or more implementations described herein, a bone pin is shown inserted through the tubular and conical tool for fixation into the spinous process.

DETAILED DESCRIPTION

One or more implementations, described herein, is a percutaneous spinal registration-and-access tool for minimally invasive spinal surgery involving lumbar pedicle screw fixation and registration (which is the set-up process for spinal computer navigation). This new tool reduces the existing invasiveness of minimal invasive surgical (MIS) techniques for spinal surgery. Further reducing invasiveness of such MIS techniques benefits the patient by further reduction in the blood loss, tissue trauma, set-up times, hospital stays, and other complications.

During lumbar pedicle screw fixation (such as for virtual fluoroscopy), a bone pin (i.e., registration pin, screw or clamp) is attached to the spine. More specifically, it is attached to a "spinous process" of one or more vertebra of the spine. The "spinous process" is a projection of bone that extends posteriorly from the lateral margin of the dorsal surface of each vertebra. In conventional approaches, an incision is made for each bone pin and then that incision is spread wide by fingers or tiny retractors. With conventional approaches, the incision must be spread wide enough for the surgeon to see, guide, and attach the reference screw to the spinous process of the vertebral spine.

However, with one or more implementations of the percutaneous spinal registration-and-access tool, the tool is inserted into a small midline incision (e.g., 1 cm) rather than the incision being manually spread wide by fingers or retractors. This tool is a conically and cylindrically shaped rigid cannula and spreads the tissue apart only as much as is necessary for insertion into the incision. The tool is configured to gently "snap" onto the spinous process. Once inserted and fixed to the spinous process, the tool provides a seamless guide tube for the optimal bone pin placement for the registration process.

This percutaneous spinal registration-and-access tool replaces the difficulty of spreading the incision with tiny retractors or fingers and the tool provides a barrier between the sharp edges of the bone pin that may tear into the surrounding soft tissue during registration pin implantation and removal as well as a thermal barrier.

This percutaneous spinal registration-and-access tool is likely to decrease complication rates of a non-securely placed bone pin and instead improve placement for a successful registration. The tool will also assist the surgeon to target the spinous process and guide the bone pin at the optimal angle for a better placement. Additionally, the tool will serve as a protective barrier between the sharp bone pin and surrounding soft tissue. In addition it is radioulcent for clear views of the spinal segments during surgical x-ray updates.

Exemplary Percutaneous Spinal Registration-and-Access Tool

FIGS. 1-3 show multiple views of exemplary percutaneous spinal registration-and-access tool 100 for minimally invasive spinal surgery involving lumbar pedicle screw fixation. The same references numbers are used in FIGS. 1-3 to refer to the same parts of the tool 100. For discussion purposes, the tool 100 is described with reference to FIGS. 1-3.

As depicted in FIGS. 1-3, the exemplary percutaneous spinal registration-and-access tool 100 is a self-retaining conical (and/or cylindrical) and largely rigid hollow tube (e.g., cannula). One or more implementations of tool 100 is constructed from radiouleny material, such as a radiolucent polymer. This way the tool 100 will not interfere with fluoroscopy. Also, a low-cost material is desirable so that the tool 100 may be a sterile-packaged single-use disposable medical device. Of course, other material that is radiouleny and/or low-cost may be used for other implementations.

The tool 100 has a proximal end 110 with a tubular opening defined by a circular proximal rim 112. The tubular opening formed by the circular proximal rim 112 forms an opening which is wide enough to easily accommodate manual insertion of a bone pin driver and reference bone pin there through. As depicted, the opening formed by the circular proximal rim 112 has a diameter of approximately 15 mm. The proximal end 110 has a finger tab 114 to provide a convenient hold for the surgeon to and maneuver the tool 100.

The tool 100 has a principal tubular body 120 (or cannula) that has a gentle taper towards an open distal end 130. As depicted, from one end to the other, the tapered tubular body 120 is approximately 22.5 mm long. While other implementations might have a non-tapered cylindrical shape, the implementation depicted in FIGS. 1-3 does have a slight taper from the proximal to distal ends and thus a generally conical shape. This shape eases the insertion into and the removal from the tissue.

Herein, "proximal" refers to the potion of the tool which is typically closest to the surgeon during surgery or, alternatively, the portion of the tool which is protruding from the body during surgery. Thus, the proximal end 110 of the tool 100 is the portion of the tool which protrudes from the body during use. Conversely, "distal" refers to the portion of the tool which is typically furthest away from the surgeon during surgery or, alternatively, the portion of the tool which is typically and primarily inside the body during surgery. Thus, the distal end 130 of the tool 100 is the portion of the tool which is inside the body during use.

At the open distal end 130, the open tube flares into two lateral bi-valved flanges 132 and 134. The term "bi-valved" is used herein in a manner similar to the context of surgical endoscopes or retractor technology when one refers to a split-lumen or a tube that has been separated and can move together or independent of the opposite retractor blade. As described herein, the two blades or flanges 132 and 134 are flexible and are open on the sides.

These lateral flanges are intended to aid in guiding the tool 100 through the tissue and onto the plateau of the spinous process. These flanges 132 and 134 are spring-biased so as to "grip" the spinous process when in use. In addition to gripping, the spring-biased lateral flanges allow the surgeon to maneuver the tool for better targeting of the spinous process without slipping off the bone. The ends of each flanges 132 and 134 —have blunt lips 136 and 138. These blunt lips are designed to minimize soft tissue resistance and no injury as the tool is passed down through the fascia (i.e., the flat layers of fibrous tissue that separate different layers of tissue), over the bone and between the paraspinous muscles (that is, those muscles around the spinous process).

The open distal end 130 of the tool 100 defines a circular cavity 140 which is designed to receive the bulbous-shaped spinous process plateau, while the lateral flanges 132 and 134 grip and stabilize the tool 100 from below.

Percutaneous Spinal Registration-And-Access Tool in Action

FIGS. 4-7 shows the exemplary percutaneous spinal registration-and-access tool 100 in action. For discussion purposes, the use of the tool 100 is described with reference to FIGS. 1-3 and FIGS. 4-7. Also for discussion purposes, particular components are indicated as performing particular functions; however, it is possible that other components (or combinations of components) may perform the particular functions.

FIG. 4 shows the lower portion of the exemplary percutaneous spinal registration-and-access tool 100 and a cross-section view 200 of a vertebra 210—particularly, its spinous process 220—and of tissue surrounding the spinous process. This tissue include the skin and fascia 230 and the paraspinous muscles 240. As depicted in FIG. 4, there is an incision 232 in the skin and fascia 230 through which the tool 100 may be inserted.

FIG. 5 shows the same elements as shown in FIG. 4, but the tool 100 is partially inserted into the patient's body. The blunt lips of the lateral flanges 132 and 134 are inserted through the incision 232 in the skin and fascia 230. The surgeon aims the tool so that the bulbous end 222 of the spinous process 220 goes in between the flanges 132 and 134. The flanges are slightly spring-biased and give way to the bulbous end 222 of the spinous process 220. Also, the spring-biased flanges gently dilate the surrounding tissue (e.g., the skin 230 and the paraspinous muscles 240) as the flanges slide over and around the spinous process 220. Once in position, the spring-biased flanges 132 and 134 capture the spinous process 220 in the area between the flanges.

As the tool 100 is passed percutaneously (i.e., through the skin/tissue) over the spinous process, the two flanges 132 and 134 flare out from approximately 2.4 mm in the closed position and over 50% of the lateral wall of the spinous process and expands up to approximately 8-10 mm. This action functionally serves to both grip and stabilize the tool 100 over the lateral cortexes of the bone.

FIG. 6 shows the same elements as shown in FIGS. 4 and 5, but the tool 100 is fully inserted into the patient's body. As depicted, the bulbous end 222 of the spinous process 220 is received by the circular cavity 136 of the tool 100 and the spinous process is gripped by the spring-biased flanges 132 and 134. The circular cavity 140 is designed to receive the bulbous end 222 of the spinous process 220. The spring-biased lateral flanges 132 and 134 grip and stabilize the tool 100. As depicted, the spring-biased lateral flanges 132 and 134 may extend to the base of the spinous process 220. However, under differing conditions (e.g., variations in human anatomy) and with different embodiments, the spring-biased lateral flanges 132 and 134 might not extend all the way down to the base of the spinous process 220.

FIG. 7 shows the same elements as shown in FIG. 6. Unlike the previous figures, FIG. 7 illustrates the use of the tool 100 for one of its primary purpose (with at least one implementation). As depicted, a screw/bone pin 300 is shown inside of the tube formed by the tool 100 itself. The tool allows for seamless passage and access of a screw/bone pin 300 and its driver (not shown) to the spinous process. With this access, the surgeon firmly affixes the screw/bone pin 300 to the bulbous end 222 of the spinous process 220. Once the screw/bone pin 300 is in place rigidly, a reference array (e.g., navigational transmitter) is attached to the pin for the navigational registration process.

When the surgeon wishes to remove the tool 100, she simply manually extracts it. The tool is not affixed to the spinous process 220 in a permanent manner like would be the case for an invasive (e.g., screw, staple, etc.) or chemical (e.g., adhesive) attachment mechanism. Instead, the tool 100 is only "gripping" the spinous process 220. As such, a gentle tug will flare-out the flanges 132 and 134 and dilate the tissue. Then the tool is easily extracted.

Other Applications, Implementations, and Details

The discussion herein focuses on the specifics of minimally invasive spinal surgery involving lumbar pedicle screw fixation. However, the tool may be used in many other surgical techniques. Some of those include (but are not limited to): Percutaneous Pedicle Screw Implantation and Fusion, Kyphoplasty, Vertebroplasty, Bone Marrow Aspiration, Bone Biopsy, Micro-Endoscopic Diskectomy and other MIS spinal implantations for interbody fusions including PLIF, TLIF, Facet screws and future—approaches approaches to the diskspace for various device implants or resection tools.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

The invention claimed is:

1. A percutaneous spinal registration-and-access tool for minimally invasive spinal surgery comprising:
    a conically shaped tubular body having a proximal end, a distal end, and a longitudinal axis extending there between, wherein both the proximal end and the distal end are open; and
    at least two flexible lateral flanges positioned opposite each other and spaced apart from each other, where when viewed in a cross sectional plane taken along the longitudinal axis, the at least two flexible lateral flanges extend downwardly and inwardly from the distal end of the conically shaped tubular body towards each other forming an open gripping area therebetween;
    wherein the at least two flexible lateral flanges form a circular cavity at the distal end of the conically shaped tubular body for receiving a bulbous end of a spinous process of a vertebra therein;
    wherein the at least two flexible lateral flanges have spaced-apart distal ends that flare outwardly and upwardly away from each other forming a smooth rounded opening between the spaced-apart distal ends; and
    wherein the circular cavity at the distal end of the conically shaped tubular body is larger than the smooth rounded opening between the spaced-apart distal ends of the at least two flexible lateral flanges.

2. The tool as recited in claim 1, wherein the at least two flexible lateral flanges are configured to grip a spinous process of a vertebra between the open gripping area between the at least two lateral flanges.

3. The tool as recited in claim 1, wherein the conically shaped tubular body is a hollow tube configured to provide access to a spinous process of a vertebra when the tool is inserted percutaneously and the spinous process is captured in the open gripping area between the at least two flexible lateral flanges.

4. The tool as recited in claim 1, further comprising a finger tab extending outwardly from the proximal end of the conically shaped tubular body.

5. The tool as recited in claim 1, wherein the tool is constructed from a radioulency material.

6. A tool for minimally invasive spinal surgery comprising:
a hollow tubular body having an open proximal end, an open distal end, and a longitudinal axis extending therebetween; and
at least two flexible spaced-apart flanges positioned opposite each other, the at least two flexible spaced-apart lateral flanges extend downwardly and inwardly from the open distal end of the hollow tubular body towards each other when viewed in a cross sectional plane taken along the longitudinal axis, and the at least two flexible spaced-apart lateral flanges forming an open gripping area there between;
wherein the at least two flexible spaced-apart flanges form a circular cavity between the at least two flexible spaced-apart flanges at the distal end of the hollow tubular body for receiving a bulbous end of a spinous process of a vertebra therein;
wherein the at least two flexible spaced-apart flanges include spaced-apart distal ends that flare outwardly and upwardly away from each other forming a smooth rounded opening between the spaced-apart distal ends; and
wherein the circular cavity between the at least two flexible spaced-apart flanges at the distal end of the hollow tubular body is larger than the smooth rounded opening between the spaced-apart distal ends of the at least two flexible spaced-apart flanges.

7. The tool as recited in claim 6, wherein the hollow tubular body is conically shaped having a narrowing diameter from the proximal end to the distal end.

8. The tool as recited in claim 6, wherein the at least two flexible spaced-apart flanges are spring-biased.

9. The tool as recited in claim 1, wherein the at least two flexible lateral flanges are spring-biased.

10. A method for using a percutaneous spinal registration-and-access tool, the method comprising:
providing the percutaneous spinal registration-and-access tool, wherein the tool comprises:
a conically shaped tubular body having a proximal end, a distal end, and a longitudinal axis extending there between, wherein both the proximal end and the distal end are open; and
at least two flexible lateral flanges positioned opposite each other and spaced apart from each other, where when viewed in a cross sectional plane taken along the longitudinal axis, the at least two flexible lateral flanges extend downwardly and inwardly from the distal end of the conically shaped tubular body towards each other forming an open gripping area therebetween;
wherein the at least two flexible lateral flanges form a circular cavity at the distal end of the conically shaped tubular body for receiving a bulbous end of a spinous process of a vertebra therein;
wherein the at least two flexible lateral flanges have spaced-apart distal ends that flare outwardly and upwardly away from each other forming a smooth rounded opening between the spaced-apart distal ends; and
wherein the circular cavity at the distal end of the conically shaped tubular body is larger than the smooth rounded opening between the spaced-apart distal ends of the at least two flexible lateral flanges;
inserting a distal end of the tool into an incision of a patient;
positioning the at least two spaced-apart flanges around a bulbous end of a spinous process of a vertebra, wherein the spinous process is gripped by the at least two spaced-apart flanges; and
inserting a registration tool with a bone pin attached to one end thereof through a hollow tubular body of the tool for affixing the bone pin to the bulbous end of the spinous process.

11. The method of claim 10, wherein the body of the tool is configured to provide access to a spinous process of a vertebra when the tool is inserted percutaneously through the incision of the patient and the spinous process is positioned between the at least two spaced-apart flanges.

12. The method of claim 10, wherein the circular cavity configured is for receiving the bulbous end of the spinous process of the vertebra.

* * * * *